United States Patent [19]

Gallo-Torres et al.

[11] 4,104,285

[45] Aug. 1, 1978

[54] TAURINE AND GLYCINE DERIVATIVES

[75] Inventors: Hugo Gallo-Torres, Livingston; Robert William Guthrie, Fairfield; James Guthrie Hamilton, Nutley; Richard Wightman Kierstead, North Caldwell; Ann Clare Sullivan, Cedar Grove, all of N.J.

[73] Assignee: Hoffmann-La Roche Inc., Nutley, N.J.

[21] Appl. No.: 790,164

[22] Filed: Apr. 22, 1977

[51] Int. Cl.$^2$ .................................................. C07J 9/00
[52] U.S. Cl. ................................ 260/397.1; 260/397.5
[58] Field of Search ................ 260/397.1, 397.2, 397.5

[56] References Cited

U.S. PATENT DOCUMENTS

| 3,634,465 | 1/1972 | Grenda | 260/397.1 |
| 3,998,859 | 12/1976 | Chen | 260/397.2 |

*Primary Examiner*—Elbert L. Roberts
*Attorney, Agent, or Firm*—Samuel L. Welt; Bernard S. Leon; William H. Epstein

[57] ABSTRACT

Taurine and glycine derivatives of nor or bisnorcholanic acid or etiocholanic acid which are useful in increasing bile flow or decreasing lipid levels and their method of production from deoxycholic acid, including intermediates thereof.

17 Claims, No Drawings

TAURINE AND GLYCINE DERIVATIVES

SUMMARY OF INVENTION

In accordance with this invention, it has been discovered that compounds of the formula:

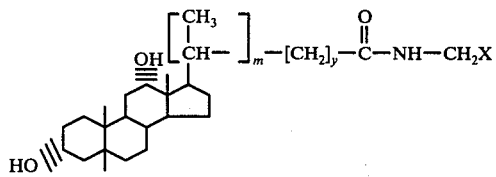

wherein X is —COOH or —CH$_2$SO$_3$H;
m and y are 0 or 1;
with the proviso that when m is 0 y is 0;
and pharmaceutically acceptable salts thereof are useful as agents for increasing bile flow or decreasing lipid levels such as triglyceride or cholesterol levels.

Of the compounds of Formula I, the compounds of Formula I where X is —CH$_2$—SO$_3$H, i.e. compounds of the formula:

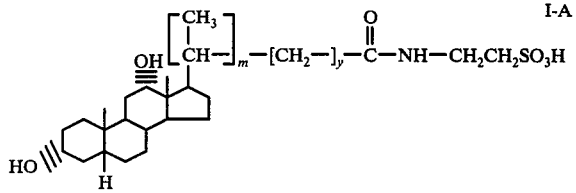

wherein m and y are as above, with the proviso that when m is 0, y is 0;
and pharmaceutically acceptable salts thereof are useful as agents for increasing bile flow.

All of the compounds of Formula I are useful as lipid lowering agents. The compound of the Formula I where X is COOH and y=0, i.e. compounds of the formula:

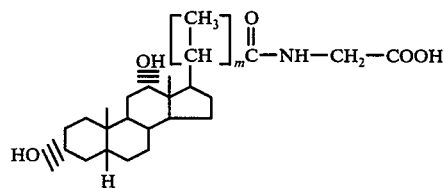

where m and X are as above
and pharmaceutically acceptable salts thereof, are useful as agents for lowering cholesterol levels.

On the other hand, compounds of the Formula I having the formula:

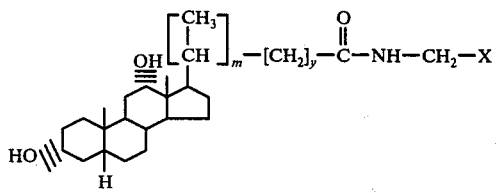

where m, y and X are as above with the proviso that when m is 0, y is 0 and with the further proviso that when m is 1 and y is 0, X is —CH$_2$SO$_3$H
and pharmaceutically acceptable salts thereof are useful as agents for lowering triglyceride levels.

The compounds of Formula I are prepared from compounds of the formula:

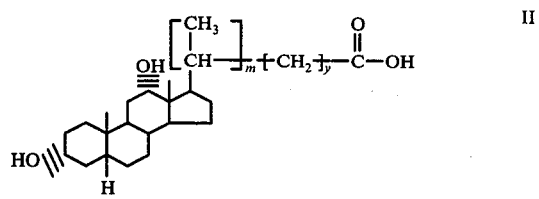

where m and y are as above the with priviso that when m is 0, y is 0;
via a reaction with glycine or taurine.

DETAILED DESCRIPTION OF THE INVENTION

As used throughout this application, the term "lower alkyl" includes both straight and branched chain alkyl groups having from 1 to 7 carbon atoms, such as methyl, ethyl, propyl, isopropylene. As used herein the term halogen or 'halide' as used herein designates all four halogen, i.e. chlorine, fluorine and bromine with chlorine being especially preferred. The term alkali metal as used herein designates all of the alkali metals such as lithium, sodium, potassium, etc. with sodium being preferred.

Where the hydroxy groups are esterified to form a hydrolyzable ester group convertible to hydroxy upon hydrolysis, these hydroxy groups can be esterified with any acid which forms an ester that can be hydrolized. Among the preferred acids which form these groups are the lower alkanoic acids which contain from 1 to 7 carbon atoms such as formic, acetic, propionic and caproic acid with formic and acetic acid being especially preferred. Other acids include aroic acids such as benzoic acid, etc.

The compounds of Formula I where X is —COOH which has the following formula

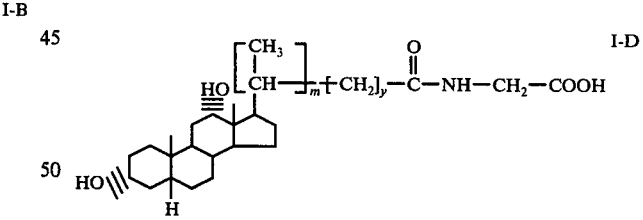

where m and y are as above in the proviso that when m is 0, y is 0
is prepared from compounds of the Formula II via the following intermediate

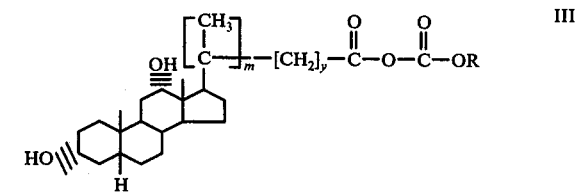

where R is lower alkyl; and m and y are as above;
with the proviso that when m is 0, y is 0.

The compound of Formula III is prepared by reacting at a temperature of from −20° C to +20° C, the compound of Formula II with a compound of the formula:

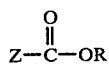

wherein R is as above, and Z is halogen in the presence of a tertiary amine. In carrying out this reaction, any conventional tertiary amine base can be utilized. Among the tertiary amine base are included tri(lower alkyl) amines such as triethylamine, tri(n-butyl)amine, tri-isopropylamine, etc. and heterocyclic amines such as pyridine. In carrying out this reaction an inert organic solvent can be used. Among the preferred solvents are the ether solvents such as dioxane, tetrahydrofuran, etc.

The compound of Formula III is converted to the compound of Formula I-D by reacting the compound of the Formula III with an aqueous solution of the sodium salt of glycine. This reaction is carried out utilizing temperatures of from −10° C to 30° C with temperatures of from 0° C to 25° C being preferred. This reaction can be carried out utilizing the same solvents used to prepare the compound of Formula III.

Where X in the compound of Formula I is —CH$_2$SO$_3$H, and m and y are 1, the resulting compounds has the formula:

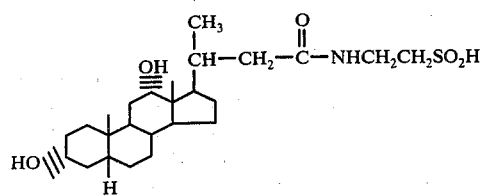

This compound is prepared from a compound of the formula

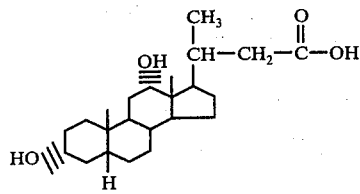

via a compound of the following

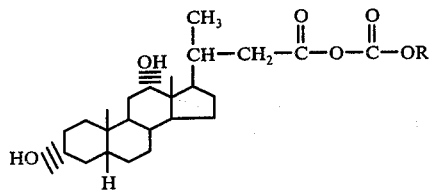

wherein R is as above.

The compound of Formula III-A is prepared from the compound of Formula II-A by reaction with the compound of Formula V in the same manner as described in connection with the formation of the compound of the Formula III from a compound of Formula II. The compound of Formula III-A is converted to a compound of the Formula I-E by reacting the compound of Formula III-A with an aqueous solution of the sodium salt of taurine. This reaction is carried out utilizing the same conditions described hereinbefore in connection with the conversion of a compound of the Formula III to a compound of the Formula I-D.

In accordance with one embodiment of the invention, the compound of Formula I-D can be prepared from the compound of Formula II via the following intermediates

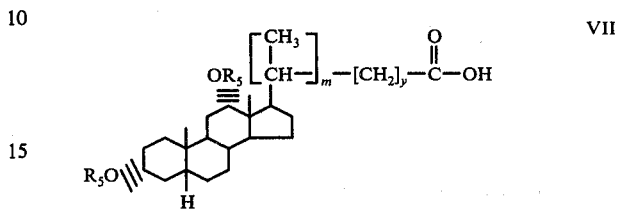

wherein R$_5$ taken together with its attached oxygen atom forms a hydrolyzable ester convertible to hydroxy by hydrolysis; m and y are as above; with the proviso that when m is 0, y is 0; and

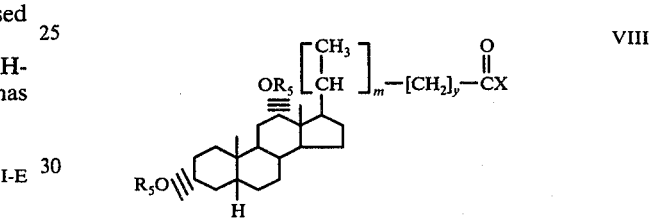

wherein R$_5$, m and y are as above; with the proviso that when m is 0, y is 0; and X is halogen and

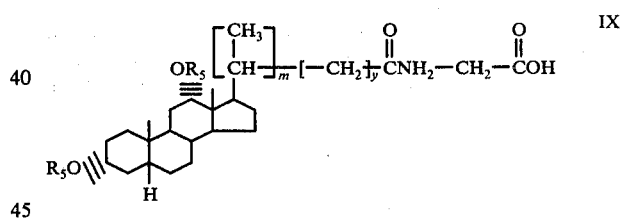

wherein R$_5$ is as above; m and y are as above, with the proviso that when m is 0, y is 0.

The compound of Formula II is converted to the compound of Formula VII by esterification. Any conventional method of esterification with an organic acid can be utilized. Therefore, the compound of Formula II can be reacted with an organic acid or reactive derivative of an organic acid such as an acid anhydride or an acid halide to form the ester of Formula VII. The ester of Formula VII is reacted with an acid halide forming agent to give the acid halide of Formula VIII. Any conventional acid halide forming agent can be utilized to carry out this reaction. Among the preferred agents are included, thionyl chloride, oxalyl chloride, etc. Any of the conditions conventional in utilizing these reagents can be utilized to affect this conversion.

The compound of Formula VIII can be converted to the compound of Formula IX by reaction with an alkali metal salt of glycine. Generally this reaction is carried out in an aqueous medium. In addition to the aqueous medium, a inert organic solvent may also be present. Any conventional inert organic solvent such as the ether solvents mentioned hereinbefore can be utilized to carry out this reaction. On the other hand, no inert organic solvent need be present in this reaction. In carrying out this reaction, any temperature of from −10° C to 30° C can be utilized.

The compound of Formula IX is converted to the compound of Formula I-D by means of basic hydrolysis. Any conventional method of basic hydrolysis can be utilized to carry out this conversion. Among the preferred methods of basic hydrolysis are included treating the compound of Formula IX with an aqueous alkali metal hydroxide such as sodium hydroxide. In carrying out this hydrolysis reaction, temperature and pressure are not critical, and this hydrolysis reaction can be carried out at room temperature and atmospheric pressure. Generally this hydrolysis reaction forms the compound of I-B in the form of its alkali metal salt. In order to form the compound of the Formula IX as a free acid, the alkali metal salt of the compound of the Formula IX formed upon hydrolysis is acidified with an inorganic acid. Any strong inorganic acid can be utilized such as aqueous hydrochloric acid, aqueous hydrobromic acid or aqueous sulfuric acid.

In accordance with another embodiment of the invention the compound of Formula VIII is converted to the compound of Formula I-D via the following intermediate

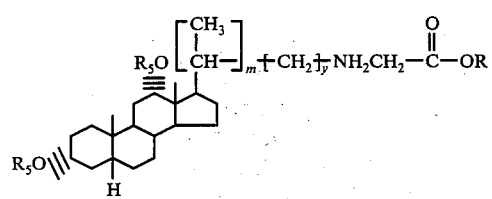

wherein $R_5$ and R are as above; and $m$ and $y$ are as above with the proviso that when $m$ is 0, $y$ is 0.

The compound of Formula VIII is converted to the compound of Formula X by reacting at a temperature of from −10° C to 30°, the compound of Formula VIII with an acid addition salt of glycine ester of the formula

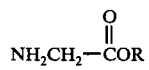

wherein R is as above.

This reaction is carried out in the presence of a tertiary amine base. Any of the tertiary amine bases such as those mentioned hereinbefore can be utilized to carry out this reaction. Generally this reaction is carried out in an inert organic solvent. Any conventional inert organic solvent can be utilized. Among the preferred inert organic solvents is included acetone. Any acid addition salt of the glycine ester can be utilized to this conversion. Among the preferred acid addition salts are the hydrohalide acid salts such as hydrochloride salts. The compound of Formula X is converted to the compound of Formula I-D by hydrolysis with a base in the manner described hereinbefore. Acidification such as described hereinbefore may be need to isolate the compound of Formula I-D as a free base.

The compound of Formula I where X is —CH$_2$CH$_2$SO$_3$H, i.e. the compound of Formula I-A can be prepared from a compound of Formula VIII via the following intermediates

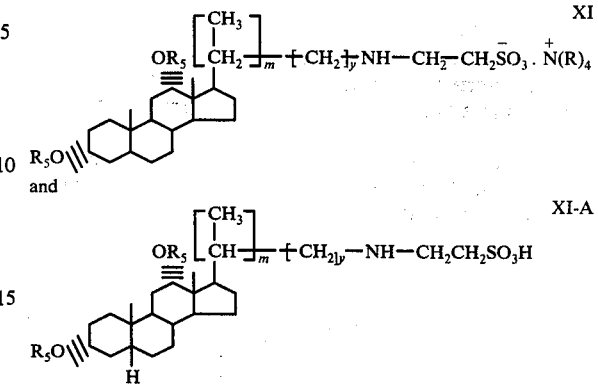

wherein $R_5$, $m$ and $y$ are as above, in the proviso that when $m$ is 0, $y$ is 0 and R is lower alkyl.

The compound of Formula VIII is converted to the compound of formula XI by reaction with lipophillic salt of taurine in an anhydrous medium. This reaction is first carried out by reacting taurine via acid intermediates of the formula with a quaternary alkyl ammonium hydroxide of the formula

(R)$_4$NOH where R is as above; preferably n-butyl to form a compound of the formula

NH$_2$CH$_2$CH$_2$S−O$_3$N+(R)$_4$  XIII

In carrying out this reaction, the taurine is first reacted with the quaternary alkyl ammonium hydroxide in an anhydrous medium to form the ammonium salt of Formula XIII. This reaction is carried out by simply reacting taurine with the ammonium hydroxide in the presence of an inert organic solvent. Any conventional inert organic solvent such as lower alkanol solvents, i.e. methanol, ethanol, etc., aromatic hydrocarbon solvents such as benzene, toluene or aliphatic hydrocarbon solvents can be utilized in forming the taurine salt. In carrying out this reaction, temperature and pressure are not critical and the taurine salt of Formula XIII can be formed at room temperature and atmospheric pressure. On the other hand, any temperature such as from 0° C to 40° C can be utilized. The salt of formula XIII is made anhydrous by removing the water formed by the reaction by azeotropic distillation with an inert organic solvent which forms an azeotropic with water.

In the next step of the invention, the compound of Formula XIII is reacted under anhydrous conditions with the compound of Formula VIII to form the compound of Formula XI. This reaction can be carried out in the presence of any conventional inert organic solvent. In carrying out this reaction, any of the conventional aromatic hydrocarbon or aliphatic hydrocarbon solvents can be utilized with benzene especially preferred. In carrying out this reaction, temperature and pressure are not critical and the reaction can be carried out at room temperature and atmospheric pressure. Generally, it is preferred to utilize the temperature of from 0° C to 40° C.

The compound of Formula XI can be converted to the compound of Formula XI-A by treatment with a strong acid. Generally this treatment is effected by passing the compound of Formula XI through a sulfonated cationic ion exchange resin. Any conventional sulfonated cationic ion exchange resin can be utilized to affect this conversion. The compound of Formula XI-A can be converted to the compound of Formula I-A by hydrolysis in a basic medium such as described hereinbefore.

In accordance with another embodiment of this invention, a method is provided for preparing a compound of the formula

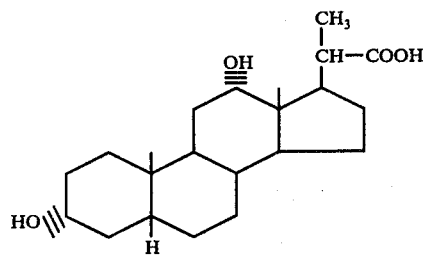

from a compound of the formula

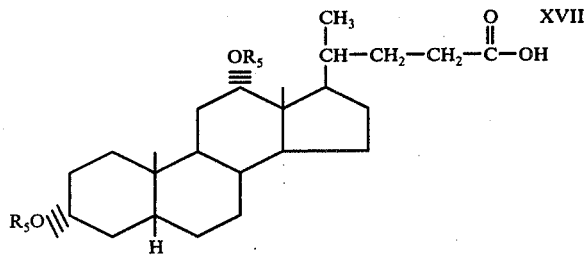

where $R_5$ is as above

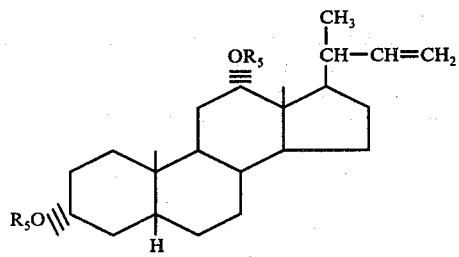

; and

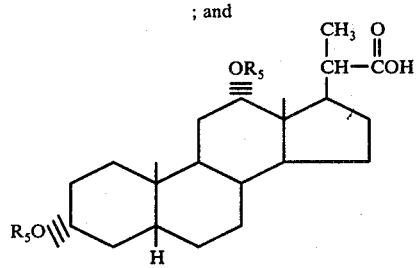

The compound of Formula XVII is converted to the compound of the Formula XVIII by treating the compound of Formula XVII with lead tetraacetate in the presence of a copper acetate catalyst. In converting the compound of Formula XVII to a compound of the Formula XVIII the lead tetraacetate generally is present in amount of at least 1 mole per mole of the compound of Formula XVII. Generally it is preferred to utilize from 1 to 3 moles of lead tetraacetate per mole of the compound of Formula XVII. On the other hand, an excess amount of lead tetraacetate, i.e. above 3 moles can be utilized. However, since no beneficial results are achieved by utilizing large amounts of lead tetraacetate, these large amounts are seldom used. The copper acetate is present in an amount of at least 0.1 mole per mole of the compound of Formula XVII. Generally it is preferred to utilize from about 0.1 to 1 mole of copper acetate per mole of the compound of Formula XVII. Again, as with lead tetraacetate, large excesses of copper acetate above 1 mole per mole of the compound of Formula XVII can be utilized. However, the large excesses of copper acetate provide no beneficial results and are therefore seldom utilized in this process. Generally this reaction is carried out in a tertiary amine base. Any of the conventional tertiary amine bases mentioned hereinbefore can be utilized in carrying out this process. Generally it is preferred to carry out this process in the presence of a heterocyclic amine base such as pyridine. The conversion of the compound of the Formula XVII to a compound of the Formula XVIII is generally carried out in the presence of an inert organic solvent. Any conventional inert organic solvent can be utilized. Among the preferred solvents are the aromatic hydrocarbon solvents such as benzene, toluene, etc. This reaction is carried out at the reflux temperature of the reaction medium.

The compound of Formula XVIII can be converted to the compound of Formula XIX by oxidation with an oxidizing agent such as potassium permanganate in acetic acid or chrominum trioxide. Any conditions conventional in utilizing such oxidizing agents can be utilized in this conversion. The compound of Formula XIX is converted to the compound of Formula II-B by hydrolysis with an aqueous alkali metal hydroxide. Any of the conditions conventional in hydrolyzing with an alkali metal hydroxide can be utilized to affect this conversion.

In accordance with another embodiment of this invention, there is provided a method for producing a compound of the formula

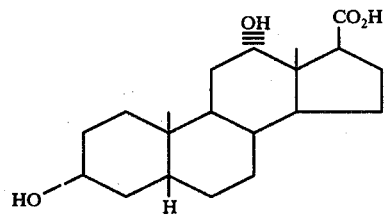

from a compound of the formula XIX via the following intermediates

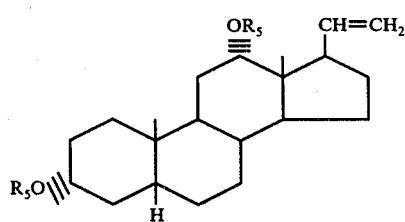

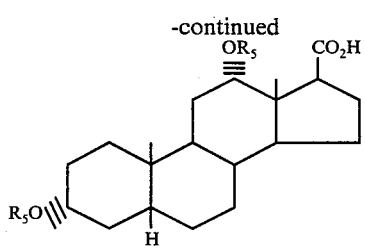

XXII

The compound of Formula XIX is converted to the compound of Formula XXI in the same manner as described in connection with the compound of Formula XVII to a compound of the Formula XVIII. The conversion of the compound of Formula XXI to a compound of Formula XXII is carried out in the same manner as described in connection with the conversion of the compound of the Formula XVIII to a compound of the Formula XIX. The conversion of the compound of the Formula XXII to a compound of the Formula II-C is carried out in the same manner as described in connection with the conversion of the compound of the Formula XIX to a compound of the Formula II-B.

The compounds of formula I-A are active in stimulation of bile flow which results in the dissolution of gall stones. This can be seen from the fact that when 100 mg of N-(3α,12α-dihydroxy-5β-24-norcholanoyl)-taurine was administered by duodenal infusion to female albino rats in a 4ml emulsion of sodium taurocholate in 85% sodium chloride, the flow of bile was increased 15% during the first 8 hours and 30% during the period of 9 to 15 hours after administration compared to the flow in rats which received only the emulsion without the taurine compound. In this study, the rats had a double catheterization of the upper part of the common bile duct. This enabled the production of lymph at a constant rate, the infusion of a bile salt and the simultaneous collection of bile.

Administration of compounds of Formula I-B result in the inhibition of activity in hypercholesteremic mammals of the rate limiting enzyme which controls the rate of cholesterol synthesis in mammals, and thus results in a lowering of the cholesterol levels of the hypercholesteremic mammal being treated. In fact, the inhibition of cholesterol synthesis results in a decrease of the natural distribution of cholesterol into the plasma and bile of the mammal being treated, and consequently will lead to a reversal of the process whereby excessive cholesterol has been previously deposited which results in the formation of cholesterol gall stones and artherosclerotic plaque. Thus, administration of the compounds of Formula I-B in the practice of this invention to hypercholesteremic mammals, will apparently lead to a depletion of excessive cholesterol deposits in the body of said mammal, for example, cholesterol gall stones and artherosclerotic plaque.

The lowering of the cholesterol levels in mammals by the administration of the compound of formula I-B can be seen from the fact that when 100mg of N-(3α,12α-dihydroxyetiocholanoyl)glycine was administered orally to female albino rats, the cholesterol level in the lymph was decreased after administration by 86% over the first 8 hours and 94% over the next 9 to 24 hr. period after administration as compared to the control. In this procedure, female albino rats (Charles River), weighing 300 ± 10 g were kept on a Purina chow diet ad libitum until the time of operation. In addition to a thoracic duct cannula, the animals had a double catheterization of the upper part of the common bile duct. This preparation enabled the production of lymph at a constant rate, the infusion of a bile salt, and the simultaneous collection of bile. All animals received, after operation, a continuous duodenal infusion of sodium taurocholate (Na-TC) in 0.85% NaCl. One day after operation, the rats were given, by stomach intubation, an emulsion containing about 4% triolein, 20 μ C of 4-$^{14}$C-cholesterol (Specific Activity 61.7 mC/mM, 159 μ C/mg), 2 mg of cholesterol, in addition to protein, carbohydrate, and saline. Both the Na-TC and the cholesterol carrier employed gave a single spot on either thin layer or glass fiber paper chromatograph so no further purification was attempted. The commercial glyceryl trioleate contained a large percentage of di- and monoolein. Triolein was, therefore, purified by passage through a silicic acid column; the final product gave a single spot on either glass fiber paper or thin layer chromatography. The radiocholesterol employed was found to be > 97% pure. To 4 ml of this emulsion was added 100 mg of either Na-TC (control group) or the compound N-(3α,12α-dihydroxyetiocholanoyl)glycine. This mixture was given orally to the animals. The sampling of thoracic duct lymph and of bile was divided into two collecting periods, 0-8 and 9-24 h after emulsion administration. Lymph specimens were lyophilized and the lipids in the residue were extracted with ethanolisopropyl ether, 2:1 parts by volume, by procedure described in Gallo-Torres, et al; Bio phys. Acta, 176 605-615 (1969). An aliquot of the lipid extract was placed on a small piece of glass fiber paper and counted. Another aliquot was used for the separation of cholesterol and its esters by glass fiber paper chromatography.

The effect of the test compounds on the appearance of total $^{14}$C-cholesterol in the thoracic duct lymph of rats was given above. Of the dose administered to the control animals, 5 × 15$^5$ dpm were recovered in the first 8 h and 3.4 × 10$^6$ dpm in the period of 9-24 h following administration of the emulsion. The tolerance of cholesterol as given above is the % decrease in the 4-$^{14}$ C-cholesterol over the control appearing in the lymph during the specified period.

The compound of Formula I-C decreases the level of lipids such as triglyceride in biological systems. The compounds of Formula I-C decrease the triglyceride levels in systems in which they are administered. Therefore, the compounds of formula I-C may be administered to hypertriglyceridemic mammals to inhibit the pancreatic lipase, the enzyme which controls the hydrolysis of triglycerides in biological systems such as mammals. Therefore, the administration of the compound of Formula I-C to biological systems results in a lowering of the triglyceride absorbed by the gastrointestinal tract. Therefore, the compounds of this invention by the inhibition of the pancreatic lipase significantly reduce the fat caloric absorption in mammals and significantly aid in the treatment of obesity.

The ability of compound I to inhibit the absorption of dietary triglyceride in rats is determined by analyzing the rise in serum triglycerides after an oral load of corn oil. For example, N-(3α,12α-dihydroxyetiocholanoyl)glycine [test compound in Table I] when administered orally to 24 hour fasted rats (6 per group) at 1.1 m moles/kg 15 minutes before a single oral dose of corn oil (20 mg/mg) demonstrated the ability of the compounds of formula I-C to inhibit absorption of triglyceride in mammals. In this procedure blood samples (0.4 ml)

were collected from the rat tail 0, 2, 4, 6, 8 and 24 hours after compound administration. Each rat is its own control. Plasma samples were analyzed for triglycerife content by the procedure set forth in Kessler and Lederer, Tehnicon Symposium 1965 Automation in Analytical Chemistry Ed L. Skeggs, published Mediad Inc. New York (1966) pp 341. The data in Table I is expressed as mg% change in plasma triglyceride levels compared to zero time control values at each time interval. This change in plasma triglycerides was determined by calculating the difference between the triglyceride level at each time point compared to zero time contol level.

Table I
EFFECT OF TEST COMPOUND ON TRIGLYCERIDE ABSORPTION IN VIVO

| Treatment | Change in Plasma Triglyceride Levels (mg %) | | | | |
|---|---|---|---|---|---|
| | 2 hr | 4 hr | 6 hr | 8 hr | 24 hr |
| Control | 35 ± 8 | 98 ± 31 | 161 ± 28 | 391 ± 58 | 130 ± 36 |
| Compound | 29 ± 3 | 107 ± 17 | 130 ± 17 | 167 ± 22 | 46 ± 5 |

The compound of Formula I may be utilized in the form of a pharmaceutically acceptable non-toxic basic salts. Preferred salts for this purpose include the alkali metals, e.g., sodium or potassium; the alkaline earth metals, e.g. calcium or complex salts such as ammonium or substituted ammonium salts such as ammonia, di- or tri-alkyl ammonium salt or a mono, di- or tri-hydroxyalkyl ammonium salt. The compounds of Formula I can be utilized in the form of conventional pharmaceutical preparations; for example, the aforesaid compounds can be mixed with conventional inorganic inert pharmaceutical carriers suitable for parenteral or enteral administration such as, for example, water, gelatin, lactose, starch, magnesium stearate, talc, vegetable oil, gums or the like. They can be administered in conventional pharmaceutical forms, e.g., solid forms, for example, tablets, dragees, capsules, suppositories or the like; or in liquid forms, for example, suspensions or emulsions. Moreover, the pharmaceutical compositions contain compounds of this invention can be subjected to conventional pharmaceutical expedients such as sterilization, and can contain conventional pharmaceutical excipients such as preservatives.

EXAMPLE 1

N-(3α,12α-Dihydroxy-5β-24-norcholanoyl)-glycine

To a solution of 3α,12α-dihydroxy-5β-24-norcholanic acid (9.87 g) in dry dioxane (50 ml) and tri-n-butylamine (6.2 ml) previously cooled to 10° C was added ethyl chloroformate (2.5 ml) and the mixture stirred at 10° for 45 minutes to produce 3α-12α-dihydroxy-5β-24-norcholanoyl-ethylcarbonate. To this compound, a solution of glycine (1.96 g) in 1N sodium hydroxide (25.2 ml) was added in one portion causing a vigorous evolution of gas. The cooling bath was removed and the reaction mixture was stirred for an additional 30 minutes at room temperature and then was concentrated under reduced pressure. The resulting syrup was dissolved in water (200 ml), acidified with concentrated aqueous hydrochloric acid and crystallization was induced by scratching. The white solid was recovered by filtration, washed with water and then dissolved in ethyl acetate. The dried ($Na_2SO_4$) solution was evaporated in vacuo to give 10.5 g of the crude product. Crystallization of the residue from ethanol-ethyl acetate furnished 6.1 g of N-(3α,12α-dihydroxy-5β-24-norcholanoyl)-glycine mp 214°–216° C. An additional 1.7 g, mp 213°–216° C, was recovered from the mother liquors. The analytical material was obtained from the same solvent system, mp 216.5°–218° C.

EXAMPLE 2

N-(3α,12α-Dihydroxy-5β-24-norcholanoyl)-taurine 9.87 g of 3α,12α-dihydroxy-5β-24-norcholanic acid was dissolved in 50 ml of freshly purified dioxane containing 6.2 ml tri-n-butylamine. The mixture was cooled to −12° and then 2.5 ml of ethyl chloroformate was added. After the reaction mixture was stirred at 12°–15° for 45 minutes, 3α,12α-dihydroxy-5β-24-norcholanoyl-ethylcarbonate was formed. To this compound in that reaction medium there was added a solution of 3.3 g of taurine in 25.2 ml of 1N NaOH and the stirring was continued for 2½ hours. The solvent was removed in vacuo and the oily residue was dissolved in 200 ml of $H_2O$. After acidification with HCl the mixture was extracted with 2 × 500 ml portions of EtOAc. The organic layers were backwashed in turn with 100 ml of $H_2O$. The combined aqueous layers were then placed in a liquid-liquid continuous extractor and extracted for 48 hours using diethyl ether. The ether extracted was dried and concentrated in vacuo to give 10.2 g of N-(3α,12α-dihydroxy-5β-24-norcholanoyl)-taurine as a white solid. Crystallization from ethanol-diethyl ether gave 6.4 g of N-(3α,12α-dihydroxy-5β-24-norcholanoyl)-taurine mp 227°–229° C.

EXAMPLE 3

3α,12α-Dihydroxycholanic acid, diformate

A dispersion of deoxycholic acid (1030 g; 2.63 mol) in 98% formic acid (3.72 l) was heated at 60°–70° with stirring for 2 hr. The resulting solution was allowed to cool slowly and was then left at room temperature overnight. It was then concentrated by distillation in vacuo at 40°. After 2 liters of distillate was collected, crystallization began to occur and the mixture was cooled to 15° C. The solids were then collected by filtration, washed with cold formic acid (400 ml) and dried to give 1065 g (90.5%) of 3α,12α-dihydroxycholanic acid, diformate, mp 192°–194°. Concentration of the mother liquors afforded additional material which raised the yield to about 95%.

EXAMPLE 4

3α,12α-Dihydroxy-Δ$^{22}$-24-norcholene, diformate

A stirred mixture of 3α,12α-dihydroxycholanic acid, diformate (375 g; 0.836 mol) and Cu (OAc)$_2$. $H_2O$ (37.5 g; 0.188 mole) in benzene (6.5 l) was heated to reflux under argon and 1 l. of solvent was distilled off. Pyridine (67.5 ml; 0.836 mol) was then added, followed by the portionwise addition over 2 hr of Pb (OAc)$_4$ (750 g; 1.69 mol). After the addition was complete the heating and stirring was maintained until evidence of gas evolution had ceased. Ethylene glycol (100 ml) was then added and after cooling, the mixture was transferred to a separatory funnel. It was washed in turn with water (2 × 3 l), 1N NaOH (1 × 2 l), 0.3N NaOH (1 × 2 l), 5% NaCl (1 × 2 l), 0.5N HCl (1 × 2 l) and 5% NaCl (1 × 2 l). The aqueous layers were backwashed with benzene (1 × 1.5 l). The combined benzene layers were dried (Na$_2$SO$_4$) and evaporated to dryness under reduced pressure. The resulting oily residue when dissolved in ethanol (600 ml) immediately began to deposit crystals. After storage overnight at 5°, the mixture was filtered and the solid was washed with ethanol. The filtrate and ethanol washings were concentrated and stored as mother liquor. The average yield from six such reactions was 262 g of 3α,12α-dihydroxy-Δ$^{22}$-24-norcholene, diformate, mp 124°–126°.

EXAMPLE 5

3α,12α-Dihydroxy-23,24-bisnorcholanic acid

A stirred solution of 3α,12α-diformyloxy-Δ$^{22}$-24-norcholene (200 g; 0.497 mol) in 2 l HOAc was cooled to −12°. Powdered KMnO$_4$ was added in portions of 120, 60 and 20 g at 1 hr intervals. (The initial reaction was exothermic, thus the first addition of oxidant was made over 10 mins so that the temperature did not exceed 20°.) One hr after the final portion of oxidant had been added, SO$_2$ was bubbled into the stirred and cooled reaction mixture until a color change from dark brown to creamy yellow was noted. The mixture was then poured into 4 liters of a vigorously stirred 5% by weight NaCl aqueous solution and the resulting white solid was collected by filtration and washed well with water. The air-dried solids were dissolved in ether (2 l) and the solution was washed in turn with dilute brine, 2N NaOH (1 l) and 0.5N NaOH (500 ml). The aqueous layers were backwashed in turn with ether (2 × 500 ml), and then the ether layers and the brine wash were discarded. The remaining basic layers were combined and left at room temperature for 30 mins, then were acidified using conc. HCl (200 ml). The resulting crude acid was recovered by filtration and was washed well with water. The air dried material was triturated with acetone (600 ml) to give 142 g (78.4%) of 3α,12α-dihydroxy-23,24-bisnorcholanic acid. Concentration of the triturant gave an additional 3 g (1.6%) of product.

EXAMPLE 6

3α,12α-Dihydroxypregn-20-ene, diformate

This oxidative decarboxylation of 3α,12α-dihydroxy-23,24-bisnor-cholanic acid, diformate was carried out by the procedure of Example 4 except that: the Pb(OAc)$_4$ was added over a shorter period (1 hr) and the reflux was continued for 1 hr after the addition was completed. Thus the oxidation of 375 g of 3α,12α-dihydroxy-23,24-bisnor-cholanic acid, diformate using the same quantity of reagents as in Example 4 furnished 238 g of crystalline 3α,12α-dihydroxy-pregn-20-ene, diformate, mp 109°–110°. Recrystallization from ethanol furnished the analytically pure material, mp 110°–11.5°.

EXAMPLE 7

Oxidation of 3α,12α-dihydroxypregn-ene, diformate

One part of 3α,12α-dihydroxypregn-ene, diformate was dissolved in 10 parts of HOAc at 10°–15° and was treated at 1 hr intervals with 0.6, 0.3 and 0.1 parts of powdered KMnO$_4$. Finally the mixture was decolorized using gaseous SO$_2$ and then it was poured into water. The resulting solid was collected by filtration, washed with water and air dried.

The crude material which resulted from the above oxidation of a total of 467 g of 3α,12α-dihydroxypregn-ene, diformate in three different experiments (50 g, 200 g and 217 g) was combined and dissolved in two liters of a mixture of CH$_2$Cl$_2$—CCl$_4$ (1:3 parts by volume). The solution was washed in turn with 5% by weight NaCl (500 ml), 1N aqueous HCl containing 5 g/100 ml NaHSO$_3$ (1 × l) and 5% by weight aqueous NaCl (500 ml), then was dried (Na$_2$SO$_4$) and evaporated. The resulting solid was crystallized from CCl$_4$-hexane to give 279 g of essentially pure 3α,12α-dihydroxyetiocholanic acid, diformate. Recrystallization from acetonehexane furnished 227.6 g of pure material. The solutions from which the product was crystallized and the washings were combined as mother liquors.

The combined mother liquors were concentrated to dryness and then were dissolved in ether (1.5 l). The solution was extracted in turn with 1.5N aqueous NaOH (1.7 l) and with 0.7N NaOH (0.6 l). The basic extracts were backwashed with ether (1 × 750 ml) and then were combined and set aside for 2 hr. The extracts were acidified using conc. aqueous HCl (300 ml) and the resulting colorless acid was collected by filtration and washed with water. After drying in vacuo over P$_2$O$_5$ the so obtained 3α,12α-dihydroxyetiocholanic acid weighed 119.7 g.

EXAMPLE 8

Methyl-N-[3α,12α-Diformyloxy-23,24-bisnor-cholanoyl]-glycinate

A solution of 3α,12α-dihydroxy-23,24-bisnorcholanic acid, diformate (32.0 g; 76.2 mmol) in SOCl$_2$ (75 ml) was left overnight at room temperature. The excess reagent was evaporated in vacuo and the last traces of SOCl$_2$ were removed by the repeated evaporation of the residue from dry benzene leaving 3α,12α,diformyloxy-23,24-bisnorcholanoylchloride. This acid chloride was dissolved in dry acetone (300 ml) and finely powdered glycine methyl ester hydrochloride (14.4 g; 114.7 mmol) was added followed by triethylamine (38.5 g; 380 mmol). The mixture was stirred at 10°–15° for 2 minutes and then diluted with water (40 ml). After 10 minutes conc. aqueous HCl (32 ml) was carefully added and the acetone was then removed under reduced pressure. The residual mass was diluted with water and extracted with benzene (2 × 300 ml). The organic extracts were washed in turn with water, 1N NaOH (1 × 100 ml) and with water, then were combined, dried (Na$_2$SO$_4$) and concentrated in vacuo. The resulting oil was triturated with ether (75 ml) yielding a solid which was collected by filtration and washed with ether to give 32.5 g (87%) of methyl-N-[3α,12α-diformyloxy-23,24-bisnor-cholanoyl]-glycinate, mp 184°–186°. Recrystallization of a small portion from acetone-hexane furnished the analytically pure methyl-N-[3α,12α-diformyloxy-23,24-bisnorcholanoyl]-glycinate, mp 189.5°–191°.

EXAMPLE 9

Methyl-N-[3α,12α-diformyloxyetiocholanic acid]-glycinate

This preparation was carried out in Example 8. Thus 59 g (150 mmol) of 3α,12α-dihydroxyetiocholanic acid diformate was converted to 3α,12α,diformyloxyetiocholanoyl chloride using 150 ml SOCl$_2$ at room temperature for 2 hours. This acid chloride was dissolved in dry acetone (500 ml) and treated in turn with powdered glycine methyl ester hydrochloride (30 g; 240 mmol) and with triethylamine (75 g; 740 mmol). After stirring at −18° for 2 minutes, water (40 ml) was added and then after a further 20 minutes the mixture was concentrated in vacuo to remove the acetone and triethylamine. The residue was partitioned between benzene (600 ml) and water (250 ml). The benzene layer was washed in turn with 0.5 N aqueous HCl (250 ml), water, ice cold 0.5 N NaOH (100 ml) and water (3 × 200 ml). The aqueous layers were backwashed in a countercurrent manner with benzene (200 ml). The combined benzene layers were dried (Na$_2$SO$_4$) and evaporated in vacuo to give 78 g of methyl-N-[3α,12α-diformyloxyetiocholanic acid]-glycinate as an oil.

EXAMPLE 10

N-(3α,12α-dihydroxy-23,24-bisnorcholanoyl)-glycine

A solution of 125 g (0.254 mol) of methyl-N-[3α,12α-diformyloxy-23,24-bisnor cholanoyl]-glycinate in 200 ml of methanol was added to a solution of 35 g (0.875 mol) NaOH in water (200 ml). After 90 minutes at room temperature the solution was concentrated in vacuo to remove the methanol and then it was poured into a mixture of conc. HCl (80 ml; 0.96 mol) in water (400 ml). The resulting crude acide was collected by filtration and washed with water (6 l). The air dried solids were dissolved in a solution of 10 g (0.25 mol) NaOH in 300 mls of water (the addition of a small amount of ethanol was necessary to achieve complete solution). After the mixture was adjusted to pH 8.9 using a small volume of 1 N NaOH, it was concentrated to dryness in vacuo. The crude sodium salt was dissolved in 1 liter of hot 95% by weight EtOH and 1 liter of hot EtOAc was added to the boiling solution. Crystals of the sodium salt of N-(3α,12α-dihydroxy-23,24-bisnorcholanoyl)-glycine formed spontaneously and the mixture was chilled at 0°-5° C overnight. This sodium salt, as a white crystalline material, was collected by filtration and after extensive drying weighed 99 g.

A solution of 500 mg of the above sodium salt in 5 mls of water was treated with 2 ml 1 N HCl and the resulting solid was collected by filtration and dried to give 420 mg of the N-(3α,12α-dihydroxy-23,24-bisnorcholanoyl)-glycine. This material after crystallization from EtOAc melted at 208°-210°.

EXAMPLE 11

N-(3α,12α-dihydroxyetiocholanoyl)glycine

A solution of 78 g of methyl-N-[3α,12α-diformyloxyetiocholanoyl]-glycine in 100 ml of methanol was mixed with a solution of NaOH 20 g (0.5 mol) in water (100 ml). After standing at room temperature for 90 minutes the mixture was concentrated in vacuo to remove the methanol. The remaining aqueous solution was acidified with a mixture of conc. HCl (43 ml; 516 mmol) in water (100 ml). The resulting crude N-(3α,12α-dihydroxyetiocholanoyl)glycine was recovered by filtration then was washed with water and air dried.

The crude solid was added portionwise to 120 ml 1 N aqueous NaOH. When dissolution of the solids became difficult the remaining material was dissolved in the minimum amount of ethanol and added to the mixture. The pH of the resulting solution was then adjusted to pH 8.7 using 1 N aqueous NaOH and then was concentrated to dryness under reduced pressure. The crude sodium salt thus obtained was dissolved in 800 ml boiling EtOH and was diluted to the cloud point with EtOAc (700 ml). The mixture was then allowed to cool to room temperature and was stored at −5° overnight. The resulting crystalline material was recovered by filtration to give 50 g of the pure sodium salt of N-(3α,12α-dihydroxyetiocholanoyl)glycine.

A solution of 375 mg of the above sodium salt in 5 ml water was treated with 2 ml 1 N HCl and the resulting solids were filtered and dried to give 308 mg of pure N-(3α,12α-dihydroxyetiocholanoyl)glycine, mp 182.5°-183°.

EXAMPLE 12

3α,12α-Diacetoxyetiocholanoyl chloride

A dispersion of 3α,12α-diacetoxyetiocholanic acid (16.8 g; 40 mmol) in thionyl chloride (30 ml) was heated to 40° to dissolve the compound and then the solution was left at room temperature for 90 minutes. The excess thionyl chloride was evaporated under reduced pressure and the last traces were removed by adding dry benzene and then evaporating the solution under reduced pressure to produce 3α,12α-diacetyoxyetiocholanoyl chloride.

EXAMPLE 13

N-(3α,12α-Dihydroetiocholanoyl)-taurine

Taurine (15.02 g; 0.12 mol) was treated with a 0.8 N tetrabutylammoniumhydroxide in methanol (150 ml; 0.12 mol). The solution was diluted with benzene (300 ml) and evaporated to dryness in vacuo. The residue was evaporated in vacuo several times from benzene to remove the last traces of water and methanol. Then, a solution of this anhydrous tetrabutylammonium salt of taurine in 150 ml of dry benzene was added in one portion to a benzene solution of the 3α,12α-diacetoxyetiocholanoyl chloride prepared in Example 12. After the resulting mixture had stirred at room temperature for 10 minutes it was evaporated to dryness under reduced pressure. The residue was dissolved in ethyl acetate and was washed (3x) with water. The aqueous washes were backwashed (2x) with ethyl acetate and then were discarded. The combined organic layers were dried and evaporated to dryness to give crude tetrabutylammonium salt of N-(3α,12α-diacetoxyetiocholanoyl)-taurine contaminated with a small amount of the salt of the starting 3α,12α-diacetoxyetiocholanic acid. The crude salt was dissolved in water and passed through a column of Amberlite 1R 120A cationic ion exchange resin (sulfonated polystyrene H+ form; 150 ml) made up in water. The eluant was extracted (2x) with ethyl acetate to remove the trace amounts of starting acid and then 80 ml 2 N NaOH was added to the aqueous phase to saponify the acetate groups. After standing overnight at room temperature the basic solution was again passed through a column of the ion exchange resin H+ form; 150 ml) and the acidic eluant was collected and concentrated in vacuo at low temperature (<35°) to 400 ml. This concentrate was then freeze dried. The resulting colorless solid was dissolved in 60 ml of hot methanol and 240 ml of hot ethyl acetate was added and the solution was immediately cooled.

After the mixture was left for 30 minutes at 0° the deposited crystalline solid was collected by filtration and washed with ethyl acetate. The material was dried in vacuo (room temperature, 0.1 mm) to constant weight to give 14.0 g of N-(3α,12α-dihydroetiocholanoyl)-taurine as its monohydrate, mp 193°-4°.

EXAMPLE 14

By the procedure of Example 12, 32.2 grams of 3α,12α-diacetoxy-24-norcholanic acid was converted to 3α,12α-diacetoxy-24-norchanoyl chloride.

EXAMPLE 15

Taurine (15.02 g; 0.12 mol) was treated with a 0.8 N tetrabutylammoniumhydroxide in methanol (150 ml; 0.12 mol). The solution was diluted with benzene (300 ml) and evaporated to dryness in vacuo. The residue was concentrated in vacuo several times from benzene to remove the last traces of water and methanol. Then, a solution of this anhydrous tetrabutylammonium salt of taurine in 150 ml of dry benzene was added in one portion to a solution of 3α,12α-diacetoxy-24-norcholanoyl-chloride in benzene. After the resulting mixture had stirred at room temperature for 10 minutes it was evaporated to dryness under reduced pressure. The residue was dissolved in ethyl acetate and was washed (3x) with water. The aqueous washes were backwashed (2x) with ethyl acetate and then were discarded. The combined organic layers were dried and evaporated to dryness to give crude tetrabutylammonium salt of N-(3α,12α-dihydroxy-24-norcholanyl)-taurine 3,12-diacetate. The crude salt was dissolved in water and passed through a column of Amberlite 1R 120A ion exchange resin ($H^+$ form; 150 ml) made up in water. The eluant was extracted (2x) with ethyl acetate to remove the trace amounts of starting acid and then 80 ml 2 N NaOH was added to the aqueous phase to saponify the acetate groups. After standing overnight at room temperature the basic solution was again passed through a column of the above ion exchange resin ($H^+$ form; 150 ml) and the acidic eluant was collected and concentrated in vacuo at low temperature (<35°) to 400 ml. This concentrate was then freeze dried. The resulting solid was dissolved in 60 ml of hot methanol and 240 ml of hot ethyl acetate was added and the solution was immediately cooled.

After the mixture was left for 30 minutes at 0° the deposited crystalline solid was collected by filtration and washed with ethyl acetate. The material was dried in vacuo at room temperature (0.1 mmHg) to constant weight to give a quantitive yield of N-(3α,12α-dihydroxy-24-norcholanoyl)-taurine 12-monoacetate. To this acetate, there was added 8 ml of 2N NaOH. After standing for 3 hours at 95° C, the basic solution was again passed through a column of the ion exchange resin ($H^+$ form; 150 ml) and the acidic eluant was collected and concentrated in vacuo at low temperature (<35°) to 400 ml. This concentrate was then freeze dried. The resulting solid was dissolved in 60 ml of hot methanol and 240 ml of hot ethyl acetate was added and the solution was immediately cooled.

After the mixture was left for 30 minutes at 0° C the deposited crystalline solid was collected by filtration and washed with ethyl acetate. The material was dried in vacuo (room temperature, 0.1 mm) to constant weight to give N-(3α,12α-dihydroxy-24-norcholanoyl)-taurine.

EXAMPLE 16

N-(3α,12α-Dihydroxy-5β-23,24-bisnorcholanoyl)-glycine 15.2 g of 3α,12α-dihydroxy-5β-23,24-bisnorcholanic acid diacetate was dissolved in 20 ml of freshly distilled thionyl chloride. The solution was left at ambient temperature for 60 minutes and then was concentrated to dryness in vacuo at room temperature. The residue was dispersed in petroleum ether (60°-80° boiling range) and again the solvent was removed in vacuo to give 17 g of the 3α,12α-dihydroxy-5β-23,24-bisnorcholanoyl chloride diacetate as a yellow foam.

Glycine (15 g) was dissolved in water (200 ml) containing 30 ml of 10 N NaOH and to this solution 17 g of the crude acid chloride was added. The mixture was stirred at room temperature for 55 hours and then was extracted (2x) with EtOAc. The aqueous layer was acidified with conc. HCl and the resulting solid was filtered and washed with water. The dried product weighed 14.6 g. Crystallization from MeOH-EtOAc (2x) gave 10.4 g of N-(3α,12α-dihyroxy-5β-23,24-bisnorcholanoyl)-glycine as a white crystalline compound, mp 185°-190°. Analytically pure material melts at 187°-192°, resolidies and remelts at 213°-215°, $[\alpha]^{25}_D$ + 42.4° (c, 1.0, MeOH). The sample contains 3/4 mole of EtOAc.

EXAMPLE 17

N-(3α,12α-Dihydroxyetiocholanoyl)-glycine 9.0 gm of 3α,12α-dihydroxyetiocholanic acid was suspended in 50 ml of freshly purified dioxane containing 6.32 ml of tri-n-butylamine. The mixture was chilled to 10° C and then 2.25 ml of ethyl chloroformate was added dropwise. After the addition was complete, the mixture was stirred at 12°-15° for 45 minutes to produce 3α,12α-dihydroxyetiocholanoylethyl carbamate. To this compound, there was added a solution of glycine (2.0 g) in 27 ml of 1 N NaOH in one portion and the stirring was continued for 2½ hours. After the addition of 100 ml of $H_2O$ the reaction mixture was concentrated to dryness in vacuo. The resulting oily residue was dissolved in water and extracted with EtOAc. The aqueous layer was acidified with concentrated HCl and the resulting gummy solid was washed with water and air-dried. This material, a mixture of starting material and the conjugate, N-(3α,12α-dihydroxyetiocholanoyl)-glycine was combined with 5.5 g of impure conjugate from a previous run and after fractional crystallization from EtOH-EtOAc furnished the pure N-(3α,12α-dihydroxyetiocholanoyl)-glycine in 2 crops: 7.0 G, mp 182°-183°; 1.65 g, mp 183°-184.5°.

EXAMPLE 18

Dietary long-chain triglycerides must be hydrolyzed by pancreatic lipase in the duodenum before absorption can occur. Compounds of formula I-C which inhibit pancreatic lipase would significantly reduce fat caloric absorption and represent useful antiobesity and hypotriglyceridemic agents. The capacity of compounds of formula I-C to inhibit rat pancreatic lipase in vitro was investigated by testing the following compounds:

Compound A = N-(3α,12α-dihydroxy-5β-24-norcholanoyl)-taurine

Compound B = N-(3α,12α-dihydroxy-5β-24-norcholanoyl)glycine

The ability of compounds to inhibit rat pancreatic lipase is determined by analyzing the nmoles of free fatty acid [oleic acid] released from [$^{14}$C]-triolein. Compounds of A and B are added to an emulsion consisting of: 200,000 dmp $^{14}$C-triolein, 7.5 mg triolein, 0.75 mg sodium taurocholate, 15 mg bovine serum albumin and 0.9 ml 0.2 M tris-HCl – 0.15 M NaCl, pH 8.6, per assay. Water and/or pancreatic lipase is added to make an assay volume of 1.0 ml. The emulsion is incubated for 20 min. at 37° C in a shaking water bath. The reaction is stopped by the addition of isopropanol; $H_2SO_4$ (40:1). The lipids are extracted twice with 3 ml volumes of hexane. The liberated fatty acids are extracted with 2 ml of 0.1 N aqueous KOH in 50% methanol. A 1 ml aliquot of the KOH layer is placed in a scintillation vial with 10 ml of 2,5-bis-2-(5-tertiary butyl benzoxazolyl)thiophene. The radioactivity is determined in a scintillation counter. Data are expressed a nmoles free fatty acid [oleic acid] related.

TABLE

INHIBITION OF RAT PANCREATIC LIPASE ACTIVITY

| Test Compound | Pancreatic Lipase Activity Ki (mM) |
|---|---|
| Compound A | 7 |
| Compound B | 8 |

EXAMPLE 19

A tablet (Wet granulation) was formulated as follows:

| Item | Ingredient | mg/Tablet |
|---|---|---|
| 1. | N-(3α,12 α-dihydroxy -5 β-24-norcholanoyl) glycine | 100 |
| 2. | Lactose | 98.5 |
| 3. | Polyvinyl pyrrolidone | 15 |
| 4. | Modified starch | 15 |
| 5. | Corn starch | 15 |
| 6. | Magnesium stearate | 1.5 |
|  | Weight of tablet | 245 mg |

Procedure:
(1) Mix items 1, 2, 4 and 5 in a suitable mixer, granulate with polyvinyl pyriolidone and dissolve in water/alcohol. Dry the granulation. Mill the dry granulation through a suitable mill.
(2) Add magnesium stearate and compress on a suitable press.

EXAMPLE 20

A tablet was formulated in the same number as in Example 19 except that the active ingredient is N-(3α,12α-dihydroxy-5β-24-norcholanoyl)taurine.

EXAMPLE 21

A tablet was formulated in the same manner as in Example 19 except that the active ingredient is N-(3α,12α-dihydroxyetiocholanoyl)-glycine.

EXAMPLE 22

A tablet (Wet granulation) was formulated as follows:

| Item | Ingredient | mg/tablet |
|---|---|---|
| 1. | N-(3α2α-dihydroxy-5β-23,24-bisnorcholanoyl)-glycine. | 100 |
| 2. | Lactose | 147.5 |
| 3. | Pregelatinized starch | 25. |
| 4. | Modified starch | 25 |
| 5. | Corn starch | 25 |
| 6. | Magnesium stearate | 2.5 |
|  | Weight of tablet | 325 |

Procedure
1. Mix items 1, 2, 3, 4 and 5 in a suitable mixer, granulate with water, and dry over night in a suitable oven. Mill through suitable mill.
2. Mix with item 6 and compress on a suitable press.

EXAMPLE 23

A capsule was formulated as follows:

| Item | Ingredient | mg/capsule |
|---|---|---|
| 1. | N-(3α,12α-dihydroxy-5β-norcholanoyl)-taurine | 100 |
| 2. | Lactose | 99 |
| 3. | Corn starch | 20 |
| 4. | Talc | 5 |
| 5. | Magnesium stearate | 1 |
|  | Fill weight of capsule | 225 |

Procedure
(1) Mix items 1, 2 and 3 in a suitable mixer. Mill through a suitable mill.
(2) Mix the mixture in Step 1 with item 4 and 5 and fill on a suitable machine.

EXAMPLE 24

A capsule was prepared by the procedure of Example 23 except that the active ingredient was N-(3α,12α-dihydroxy-5β-24-norcholanoyl)glycine.

We claim:
1. A compound of the formula

$$\left[ \begin{array}{c} CH_3 \\ | \\ CH \end{array} \right]_m - [CH_2]_y - \overset{O}{\underset{\|}{C}} - NHCH_2X$$

(with steroid nucleus bearing OR and RO substituents)

wherein R is hydrogen, lower alkanoyloxy or benzoyloxy,

X is $-COOR_1$ or $CH_2SO_3H$; $R_1$ is hydrogen or lower alkyl; $m$ and $y$ are 0 or 1 with the proviso that when $m$ is 0, $y$ is 0;

or pharmaceutically acceptable salts thereof.

2. The compound of claim 1 wherein X is $-COOR_1$.

3. The compound of claim 1 wherein said compound is N-(3α,12α-dihydroxy-5β-24-norcholanoyl)-glycine.

4. The compound of claim 1 wherein said compound is methyl-N-[3α,12α-diformyloxyetiocholanoyl]-glycinate.

5. The compound of claim 1 wherein said compound is N-(3α,12α-dihydroxyetiocholanoyl)-glycine.

6. The compound of claim 1 wherein said compound is N-(3α,12α-dihydroxy-5β-23,24-bisnorcholanoyl)-glycine.

7. The compound of claim 1 wherein X is $CH_2SO_3H$.

8. The compound of claim 7 wherein said compound is N-(3α,12α-dihydroxy-5β-24-norcholanoyl)-taurine.

9. The compound of claim 7 wherein said compound is N-(3α,12α-dihydroxy-5β-norcholanoyl)-taurine 3,12-diacetate.

10. The compound of claim 7 wherein said compound is the tetrabutyl ammonium salt of N-(3α,12α-3,12-dihydroxy-5β-24-norcholanoyl)-taurine-3,12-diacetate.

11. The compound of claim 7 wherein said compound is N-(3α,12α-dihydroxyetiocholanoyl)-taurine.

12. A compound of the formula

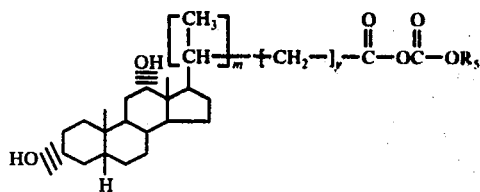

wherein $R_5$ is lower alkyl; $m$ and $y$ are 0 to 1 with the proviso that when $m$ is 0, $y$ is 0.

13. The compound of claim 12 wherein said compound is 3α,12α-dihydroxy-5β-24-norcholanoyl ethyl carbonate.

14. The compound of claim 12 wherein said compound is 3α,12α-dihydroxy-etiocholanoyl ethyl carbonate.

15. A compound of the formula:

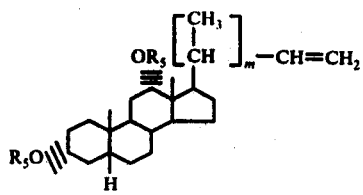

wherein $R_5$ is lower alkanoyloxy or benzoyloxy; and X is an integer from 0 to 1.

16. The compound of claim 15 where said compound is 3α,12α-dihydroxy-5β-$\Delta^{22}$24 norcholene,diformate.

17. The compound of claim 15 where said compound is 3α,12α-dihydroxy-5β-pregn-20-ene,diformate.

* * * * *

UNITED STATES PATENT AND TRADEMARK OFFICE
CERTIFICATE OF CORRECTION

PATENT NO. : 4,104,285

DATED : August 1, 1978

INVENTOR(S) : Hugo Gallo-Torres; Robert William Guthrie; James Guthrie Hamilton; Richard Wightman Kierstead; Ann Clare Sullivan It is certified that error appears in the above—identified patent and that said Letters Patent is hereby corrected as shown below:

Column 22, Claim 15,

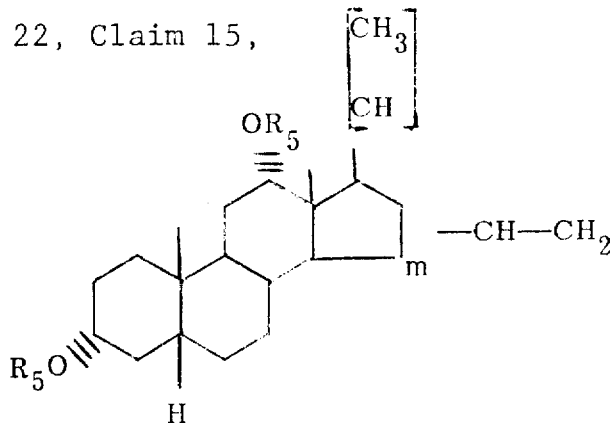

should be

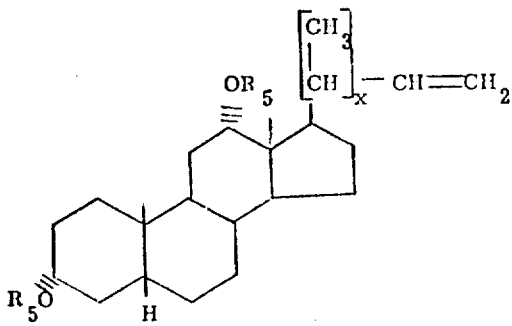

Signed and Sealed this

Fifteenth Day of December 1981

[SEAL]

Attest:

Attesting Officer

GERALD J. MOSSINGHOFF

Commissioner of Patents and Trademarks